(12) United States Patent
Moriyama

(10) Patent No.: US 8,002,697 B2
(45) Date of Patent: Aug. 23, 2011

(54) DUAL ENDOSCOPE SYSTEM WITH DISPLAY UNIT

(75) Inventor: Hiroki Moriyama, Tokyo (JP)

(73) Assignee: Olympus Corporation (JP)

( * ) Notice: Subject to any disclaimer, the term of this patent is extended or adjusted under 35 U.S.C. 154(b) by 1336 days.

(21) Appl. No.: 11/553,121

(22) Filed: Oct. 26, 2006

(65) Prior Publication Data

US 2007/0055106 A1    Mar. 8, 2007

Related U.S. Application Data

(63) Continuation of application No. PCT/JP2005/007924, filed on Apr. 26, 2005.

(30) Foreign Application Priority Data

Apr. 27, 2004    (JP) .................................. 2004-132072

(51) Int. Cl.
    *A61B 1/06*    (2006.01)
(52) U.S. Cl. ......... 600/113; 600/129; 600/177; 600/182
(58) Field of Classification Search .................. 600/113, 600/182, 176, 109, 129, 130, 173, 167, 168, 600/178, 177
    See application file for complete search history.

(56) References Cited

U.S. PATENT DOCUMENTS

| | | | | |
|---|---|---|---|---|
| 4,272,156 A | * | 6/1981 | Ishibashi et al. | 385/117 |
| 4,736,734 A | * | 4/1988 | Matsuura et al. | 600/110 |
| 5,315,383 A | | 5/1994 | Yabe et al. | |
| 5,614,943 A | | 3/1997 | Nakamura et al. | |
| 5,827,172 A | * | 10/1998 | Takahashi et al. | 600/176 |
| 5,879,288 A | * | 3/1999 | Suzuki et al. | 600/176 |
| 5,980,454 A | * | 11/1999 | Broome | 600/176 |
| 6,251,068 B1 | * | 6/2001 | Akiba et al. | 600/182 |
| 6,569,088 B2 | * | 5/2003 | Koshikawa | 600/177 |
| 7,267,647 B2 | * | 9/2007 | Okada et al. | 600/166 |
| 2003/0025789 A1 | | 2/2003 | Saito et al. | |

FOREIGN PATENT DOCUMENTS

| | | |
|---|---|---|
| EP | 1 695 653 | 8/2006 |
| JP | SH056-75909 | 6/1981 |
| JP | 04-102432 | 4/1992 |
| JP | 7-140329 A | 6/1995 |
| JP | 9-98943 A | 4/1997 |
| JP | 2000-37345 A | 2/2000 |
| JP | 2003-275165 A | 9/2003 |

OTHER PUBLICATIONS

Supplementary Euro-lean Patent Application No. Search Report dated Jun. 23, 2009 in corresponding European EP 05 73 7166 (English language).
International Search Report PCT/JP2005/007924 dated Aug. 5, 2005 (Japanese Patent Office).

* cited by examiner

*Primary Examiner* — John P Leubecker
(74) *Attorney, Agent, or Firm* — Ostrolenk Faber LLP

(57) ABSTRACT

An endoscope system includes a first endoscope having a first observation optical system with a first viewing angle and a first illumination optical system; and a second endoscope having a second observation optical system with a second viewing angle wider than the first viewing angle and a second illumination optical system. A second illumination region of illuminating light that is emitted by the second illumination optical system and has a predetermined illuminance is wider than a first illumination region of illuminating light that is emitted by the first illumination optical system and has a predetermined illuminance, at any imaging distance that is pointed in an observation direction from a distal end of an insertion portion of each of the first endoscope and the second endoscope.

5 Claims, 12 Drawing Sheets

DUAL ENDOSCOPE SYSTEM WITH DISPLAY UNIT

CROSS-REFERENCE TO RELATED APPLICATIONS

This application is a continuation of PCT international application Ser. No. PCT/JP2005/007924 filed Apr. 26, 2005 which designates the United States, incorporated herein by reference, and which claims the benefit of priority from Japanese Patent Application No. 2004-132072, filed Apr. 27, 2004, incorporated herein by reference.

BACKGROUND OF THE INVENTION

1. Field of the Invention

The present invention relates to an endoscope, and more particularly to an endoscope system including two endoscopes that are different from each other in viewing angle.

2. Description of the Related Art

Conventionally, an endoscope has been widely used in a medical field and the like. The endoscope is employed to observe organs and the like inside a body cavity by inserting an elongate insertion portion into the body cavity, and to operate various treatments by using a treatment instrument that is inserted into a treatment instrument insertion channel, if necessary. A bendable portion is provided at a distal end of the insertion portion, and an observation direction of an observation window of the distal end portion is changed by manipulating a manipulating portion of the endoscope.

A viewing angle of the conventional endoscope is, for example, 140° (degree), and an operator observes inside the body cavity by an observation image corresponding to the viewing angle. When the operator desires to observe a region outside a region corresponding to a field of view during the observation inside the body cavity, the operator can bend the bendable portion to observe such region.

On the other hand, an endoscope having a wider viewing angle has been proposed to allow an observation of a wider region. The endoscope has an advantage that the observation is easily performed and a region necessary to be treated is easily found since an imaging region is widened by having the wide viewing angle (for example, see Japanese Patent Application Laid-Open No. H4-102432).

SUMMARY OF THE INVENTION

An endoscope system according to one aspect of the present invention includes a first endoscope having a first observation optical system with a first viewing angle and a first illumination optical system; and a second endoscope having a second observation optical system with a second viewing angle wider than the first viewing angle and a second illumination optical system. A second illumination region of illuminating light that is emitted by the second illumination optical system and has a predetermined illuminance is wider than a first illumination region of illuminating light that is emitted by the first illumination optical system and has a predetermined illuminance, at any imaging distance that is pointed in an observation direction from a distal end of an insertion portion of each of the first endoscope and the second endoscope.

An endoscope according to another aspect of the present invention includes an observation optical system with a predetermined viewing angle; and plural illumination optical systems that illuminate a subject body with illuminating light. An illumination region of the illuminating light having an illuminance greater than or equal to a predetermined illuminance emitted by the plural illumination optical systems is wider than an illumination region of an illumination optical system provided in other endoscope having an observation optical system with a viewing angle narrower than the predetermined viewing angle, at any imaging distance that is pointed in an observation direction from a distal end of an insertion portion.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention are explained with reference to the drawings hereinafter.

Figure 1:
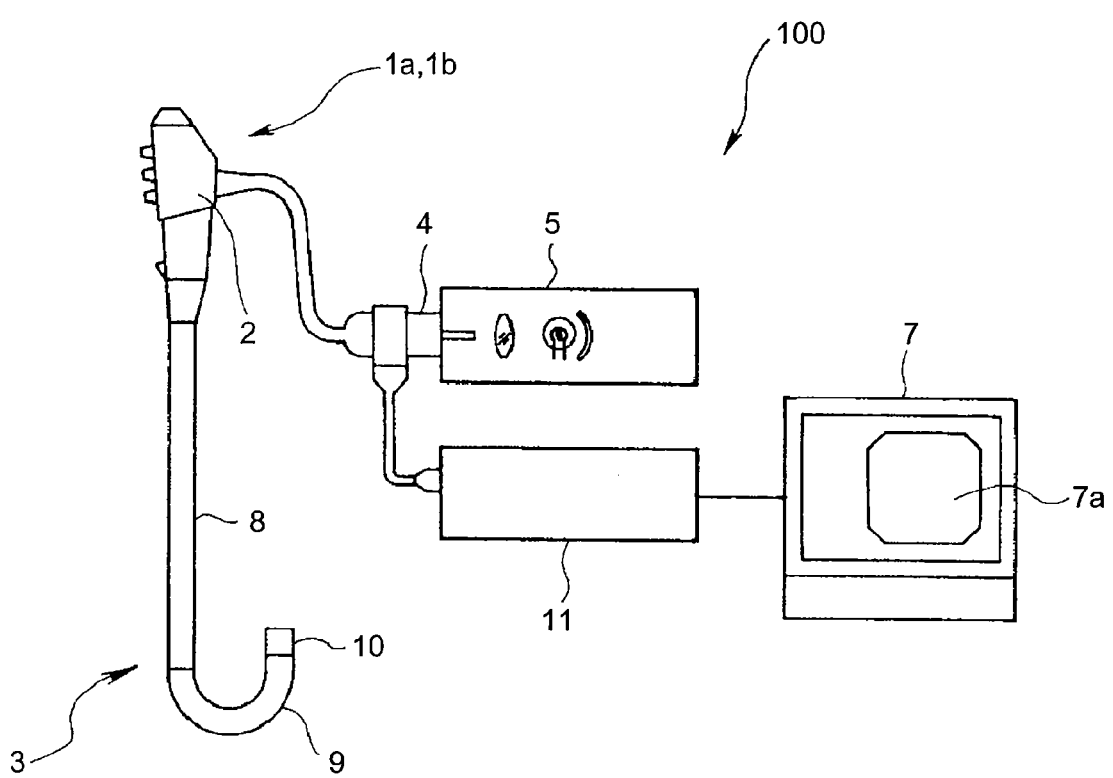
FIG. 1 is an explanatory view schematically showing an endoscope system according to a first embodiment.

A configuration of an endoscope system 100 according to the present embodiment is explained with reference to FIG. 1. FIG. 1 is an explanatory view schematically showing the endoscope system 100 according to the present embodiment of the present invention. As shown in FIG. 1, a first endoscope 1a and a second endoscope 1b (hereinafter referred to as a first endoscope 1 when the two endoscopes are not specifically distinguished) includes a manipulating portion 2, an insertion portion 3, and a universal cord 3a. The manipulating portion 2 controls bending manipulation and a channel system. The insertion portion 3 is inserted into a body cavity while a proximal end side thereof is connected to the manipulating portion 2. The universal cord 3a is extended from the manipulating portion 2, and the universal cord 3a has a connector portion 4 at a distal end thereof. The connector portion 4 is connected to a light source 5 and a processor 11, which are exterior devices, through a predetermined connector. The processor 11 is connected to a monitor 7. The first endoscope 1a and the second endoscope 1b can be connected to the processor 11 and the light source 5 through the connector if necessary, or each of the first endoscope 1a and the second endoscope 1b may be kept connected to the processor 11 and the light source 5 through the connector, and the connection to each of the endoscopes is switched by a switch not shown.

The insertion portion 3 has a flexible tube portion 8 that has flexibility, a bendable portion 9 that is provided at a distal end side of the flexible tube portion 8, and a distal end portion 10 that is provided at a distal end side of the bendable portion 9. A solid-state imaging sensor 22 (see FIG. 2) for imaging a region inside the body cavity is installed in the distal end portion 10.

Image signals of the region inside the body cavity imaged by the solid-state imaging sensor 22 that is provided in the distal end portion 10 are transmitted to the processor 11 through the universal cord 3a. As described hereinafter, the processor 11 displays an observation image of the imaged region on a monitor screen 7a of the monitor 7 based on signals that are the transmitted processed image signals. Here, the monitor 7 is a display unit that is connected to the processor 11.

A manipulating knob (not shown) employed for remotely bending the bendable portion 9 is arranged on the manipulating portion 2. A manipulating wire (not shown) that penetrates through the insertion portion 3 pulls and looses the bendable portion 9 by manipulating the manipulating knob, and as a result, the bendable portion 9 is bendable in four directions.

Figure 2:
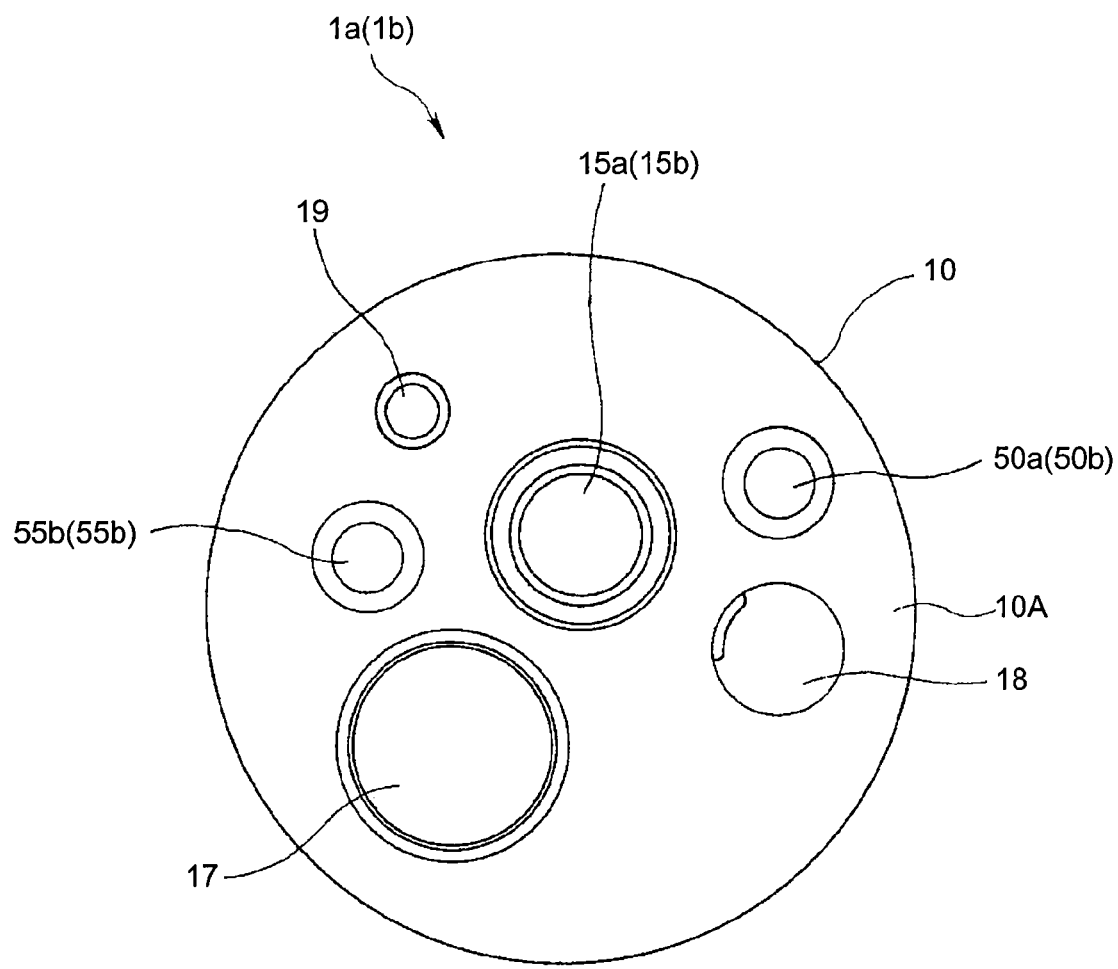
FIG. 2 is an elevational view of a distal end face of a distal end portion of an endoscope.
Figure 3:
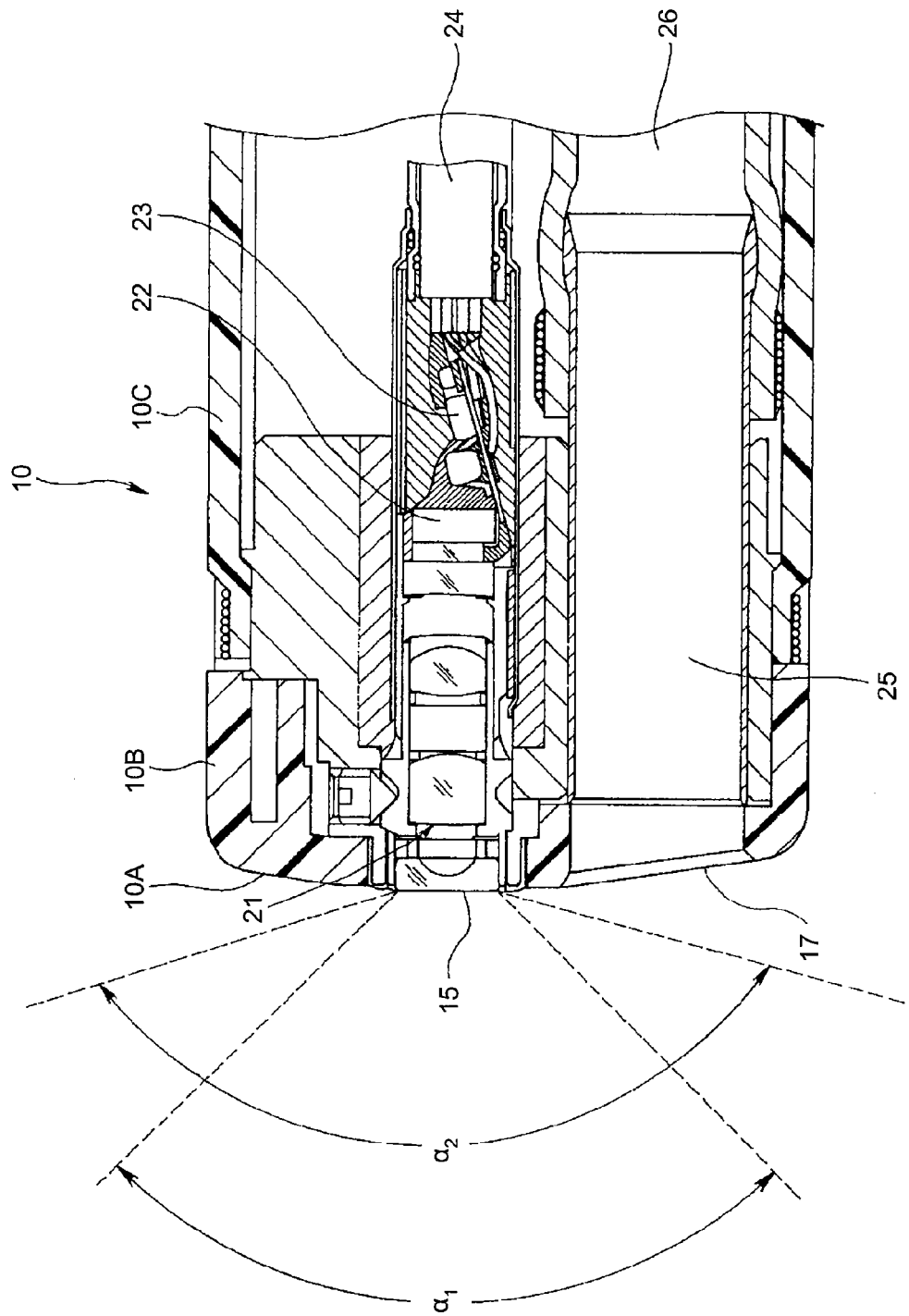
FIG. 3 is a longitudinal sectional view of the distal end portion of the endoscope.

Next, a configuration of the distal end portion 10 of the endoscope 1 is explained in details with reference to FIGS. 2 and 3. FIG. 2 is an elevational view of a distal end face 10A of the distal end portion 10 of the endoscope 1, and FIG. 3 is a sectional view of the distal end portion 10 of the endoscope 1 taken along a longitudinal direction.

As shown in FIG. 2, the distal end face 10A of the distal end portion 10 includes an observation optical member (hereinafter referred to as an observation window) 15 (let the observation window of the first endoscope 1a be a first observation window 15a, and let the observation window of the second endoscope 1b be a second observation window 15b), two illumination optical members (hereinafter referred to as illumination window) 50 and 55 (the first endoscope 1a has two illumination windows 50a and 55a, and the second endoscope 1b has two illumination windows 50b and 55b), a treatment instrument channel opening 17, an air/water nozzle 18, and a front water opening 19. The two illumination optical members 50 and 55 are arranged around the observation window, and the air/water nozzle 18 supplies air or water to the observation window 15.

Furthermore, the first endoscope 1a and the second endoscope 1b are connectable to the same exterior device. In the present embodiment, the first endoscope 1a and the second endoscope 1b are connectable to at least one of the processor 11 and the light source 5.

As shown in FIG. 3, the distal end portion 10 of the endoscope 1 is formed by a distal end cap 10B and a cylindrical exterior case 10C. Further, an observation optical system 21 (the first endoscope 1a has a viewing angle α1 of a first observation optical system 21a, and the second endoscope 1b has a viewing angle α2 of a second observation optical system 21b) having a viewing angle α, which is a fixed viewing angle or the widest viewing angle, is arranged inside the distal end portion 10 of the endoscope 1. The observation optical system 21 is formed by plural optical lenses that are arranged from the observation window 15 provided on the distal end face 10A of the distal end cap 10B toward inside the distal end portion 10. The solid-state imaging sensor 22 is arranged at a focal point of the observation optical system 21. A circuit substrate 23 having a circuit function that controls driving of the solid-state imaging sensor 22 and takes in the imaging signals on which a photoelectrical conversion is performed is connected to a rear side of the solid-state imaging sensor 22. The circuit substrate 23 has a CDS circuit 35 and an analog/digital conversion circuit 36 described hereinafter, and a signal cable 24 is connected to the circuit substrate 23. A proximal end of the signal cable 24 is connected to the processor 11.

The treatment instrument channel opening 17 that is provided on the distal end face 10A of the distal end cap 10B is connected to a treatment instrument channel 26 through a treatment instrument insertion channel 25 that is formed in a substantially cylindrical shape. Further, the first endoscope 1a can image a region corresponding to a field of view with the viewing angle α1 that is, for example, fixed at substantially 140° or the widest angle.

The observation optical system 21 having the viewing angle α2 that is larger than the viewing angle α1 of the first endoscope 1a described above is arranged in the distal end portion 10 of the second endoscope 1b (α1<α2) Here, the viewing angle α2 is, for example, fixed at substantially 170° or the widest angle. In other words, the second endoscope 1b can image a region corresponding to a field of view that is wider than the region corresponding to the field of view of the first endoscope 1a.

Figure 4:
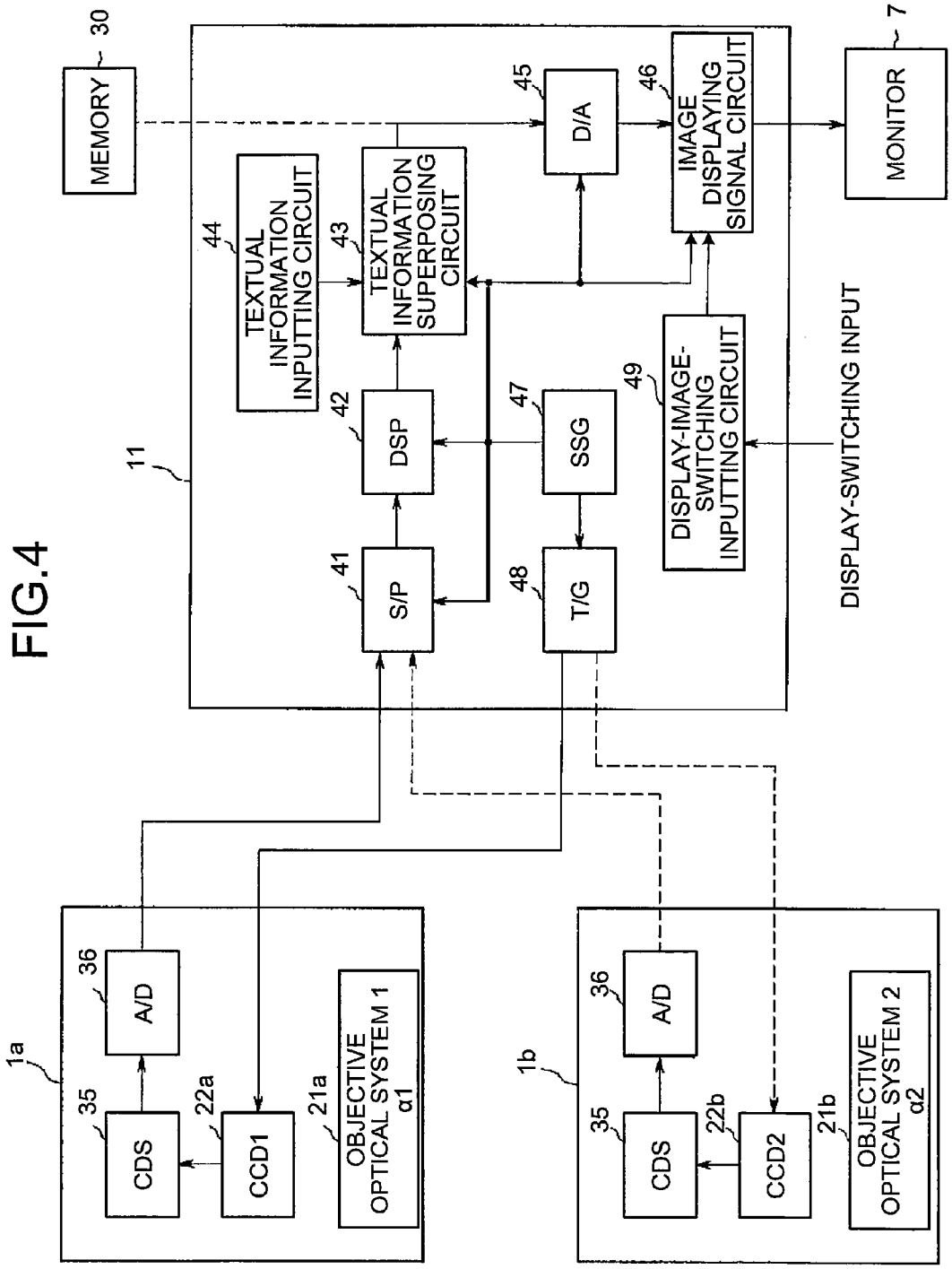
FIG. 4 is a block diagram showing a major configuration of the endoscope system according to the first embodiment.

Next, the endoscope system 100, which has the first endoscope 1a and the second endoscope 1b, according to the present embodiment is explained with reference to FIG. 4. FIG. 4 is a block diagram showing a major configuration of the endoscope system 100 according to the present embodiment.

The endoscope system 100 has the first endoscope 1a, the second endoscope 1b, the processor 11, the monitor 7, and the light source 5 (see FIG. 1). The first endoscope 1a and the second endoscope 1b are connectable to the same exterior device, and in the present embodiment, the first endoscope 1a and the second endoscope 1b are connectable to at least one of the processor 11 and the light source 5. The first endoscope 1a and the second endoscope 1b are employed (configured for observation) for a same region (for example, large intestine) in a subject body.

The first endoscope 1a has a first observation optical system 21a, a first solid-state imaging sensor (hereinafter referred to as first CCD) 22a, a CDS circuit 35, and an analog/digital conversion circuit (hereinafter referred to as A/D circuit) 36. The first observation optical system 21a is formed by plural lenses having mainly the viewing angle α1 (for example, substantially 140°). The first CCD 22a is arranged at a focal point of the first observation optical system 21a, and images the observation region. The CDS circuit 35 performs a correlated double sampling processing on the imaging signals generated by the first CCD 22a. The analog/digital conversion circuit 36 converts analog imaging signals processed at the CDS circuit 35 to digital imaging signals.

The second endoscope 1b has a second observation optical system 21b, a second solid-state imaging sensor (hereinafter referred to as second CCD) 22b, the CDS circuit 35, and the analog/digital conversion circuit 36. The second observation optical system 21b is formed by plural lenses having mainly the viewing angle α2 (for example, substantially 170°) that is larger than the viewing angle of the first observation optical system 21a of the first endoscope 1a ($\alpha 1 < \alpha 2$). The second CCD 22b is arranged at a focal point of the second observation optical system 21b, and images the observation region. The CDS circuit 35 performs the correlated double sampling processing on the imaging signals generated by the second CCD 22b. The analog/digital conversion circuit 36 converts analog imaging signals processed at the CDS circuit 35 to digital imaging signals.

The first observation optical system 21a is arranged on a central axis of the first observation window 15a described hereinbefore, and the second observation optical system 21b is arranged on a central axis of the second observation window 15b described hereinbefore. In other words, an optical axis of the first observation optical system 21a coincides with the central axis of the first observation window 15a, and an optical axis of the second observation optical system 21b coincides with the central axis of the second observation window 15b. Furthermore, the optical axis of the first observation optical system 21a is parallel to each central axis of the illumination windows 50a and 55a described hereinbefore, and the optical axis of the second observation optical system 21b is parallel to each central axis of the illumination windows 50b and 55b described hereinbefore.

The processor 11 includes a separating processing circuit (hereinafter referred to as S/P circuit) 41, a digital signal processing circuit (hereinafter referred to as DSP circuit) 42, a textual information superposing circuit 43, a textual information inputting circuit 44, a digital/analog signal conversion circuit (hereinafter referred to as D/A circuit) 45, an image displaying signal circuit 46, a reference signal generator circuit (hereinafter referred to as SSG) 47, a timing signal generator circuit (hereinafter referred to as T/G circuit) 48, and a display-image-switching inputting circuit 49.

The S/P circuit 41 separates luminance signals, color signals, and the like of the digital imaging signals from the A/D circuit 36 of the first endoscope 1a or from the A/D circuit 36 of the second endoscope 1b. The DSP 42 performs predetermined digital signal processing as well as correction processing such as white balance correction and γ correction with respect to the luminance signals and the color signals separated at the S/P circuit 41, to generate digital endoscope image signals.

The textual information superposing circuit 43 superposes textual information signals indicating patient information such as, name, age, and gender of a patient and date and time of the endoscope observation, on the digital endoscope image signals that are signals processed at the DSP circuit 42. The textual information signals that is to be superposed at the textual information superposing circuit 43 is generated from the patient information that is input by the operator through a keyboard (not shown) at the textual information inputting circuit 44. The digital endoscope image signals on which the textual information is superposed at the textual information superposing circuit 43 is converted to analog endoscope image signals at the D/A circuit 45, and then output to the image displaying signal circuit 46. Here, the digital endoscope image signals on which the generated textual information signals are superposed at the textual information superposing circuit 43 is recorded in a memory 30 that is detachably provided on the processor 11.

The image displaying signal circuit 46 converts the analog endoscope image signals supplied from the D/A circuit 45 to image signals that are employed for displaying the observation image and the patient information on the monitor 7. The image displaying signal circuit 46 changes display positions of the observation image and the patient information that are to be displayed on the monitor 7 according to control signals from the display-image-switching inputting circuit 49. A command for switching the displaying such as a command for changing the display position, not shown, of the observation image and the patient information that are to be displayed on the monitor 7 by the operator can be input into the display-image-switching inputting circuit 49.

The SSG circuit 47 generates and outputs reference signals that control drivings of the S/P circuit 41, the DSP circuit 42, the textual information superposing circuit 43, the D/A circuit 45, and the image displaying signal circuit 46. The T/G circuit 48 generates timing signals to drive control each of the first CCD 22a and the second CCD 22b of the first and the second endoscopes 1a and 1b based on the reference signals from the SSG circuit 47.

Figure 5:
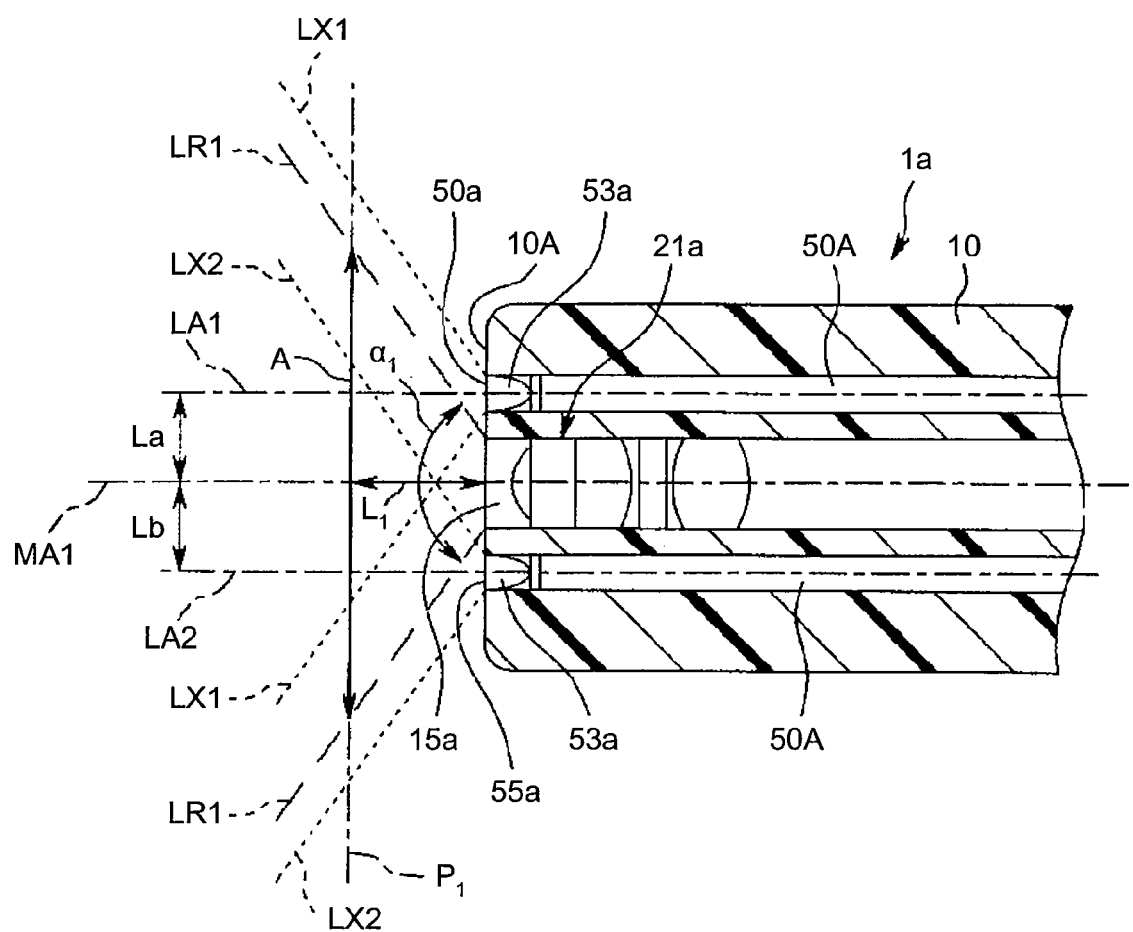
FIG. 5 is a longitudinal sectional view of the distal end portion of a first endoscope along a plane passing through each center of window faces of illumination windows and a center of a window face of a first observation window.
Figure 6:
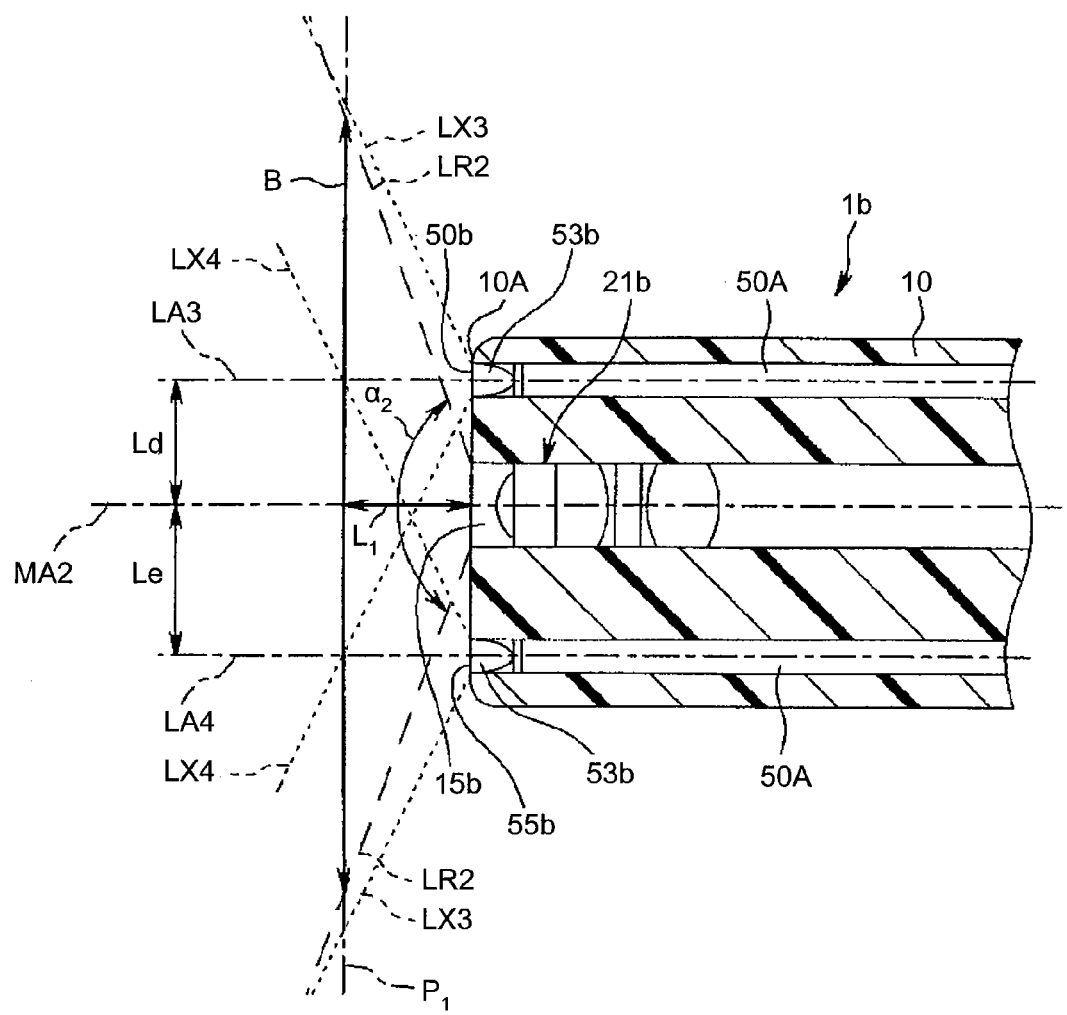
FIG. 6 is a longitudinal sectional view of the distal end portion of a second endoscope along a plane passing through each center of window faces of illumination windows and a center of a window face of a second observation window.

Next, the first endoscope 1a and the second endoscope 1b are explained further in details with reference to FIGS. 5 and 6. FIG. 5 is a longitudinal sectional view of the distal end portion 10 of the first endoscope 1a along the longitudinal direction thereof along a plane passing through each of the centers of window faces of illumination windows 50a and 55a and a center of a window face of the first observation window 15a. FIG. 6 is a longitudinal sectional view of the distal end portion 10 of the second endoscope 1b along the longitudinal direction thereof along a plane passing through each of the centers of window faces of illumination windows 50b and 55b and a center of a window face of the second observation window 15b.

In the present embodiment, as shown in FIG. 5, each of the illumination windows 50a and 55a on the distal end portion 10 of the first endoscope 1a has illumination lenses 53a. A light guide bundle 50A runs through the endoscope 1 from a proximal end of each illumination lens 53a, and the light guide bundle 50A is connected to the light source 5. Further, an illumination optical system includes the illumination windows 50a, 55a, and the illumination lens 53a, and illuminating light from the light guide bundle, which is an illuminating member, runs through the illumination optical system.

A central axis (central axis of the illumination region of the illuminating light) of the illumination window 50a of the first endoscope 1a is arranged at a position so as to be separated by a predetermined length La from a central axis, which is an optical axis of the first observation window 15a. The illumination window 55a of the first endoscope 1a is arranged at a position so as to be separated by a predetermined length Lb from the central axis of the first observation window 15a. Further, the central axis of the first observation window 15a coincides with an optical axis MA1 of a first observation optical system 21a. Furthermore, the central axis of the illumination window 50a coincides with a central axis LA1 of the illumination region of the illuminating light, and the central axis of the illumination window 55a coincides with a central axis LA2 of the illumination region of the illuminating light. In other words, the central axis LA1 and the optical axis MA1 are separated by the predetermined length La, and the central axis LA2 and the optical axis MA1 are separated by the predetermined length Lb. The lengths La and Lb can be the same (La=Lb), or can be different (La≠Lb).

Further, in the first endoscope 1a, the light guide bundle 50A that is to be bundled runs through the insertion portion 3 and the universal cord 3a from each lens face of a proximal end side of the illumination lenses 53a to the connector portion 4. The light guide bundle 50A that runs to the connector portion 4 is connected to the light source 5 by the connector portion 4 described above. The illuminating light that is supplied from the light source 5 is emitted from two distal end faces of the light guide bundle 50A. Then, the illuminating light having the central axis LA1 that passes through the illumination lens 53a is emitted from the illumination window 50a. Similarly, the illuminating light having the central axis LA2 that passes through the illumination lens 53a is emitted from the illumination window 55a.

In the present embodiment, as shown in FIG. 6, each of the illumination windows 50b and 55b on the distal end portion 10 of the second endoscope 1b has illumination lenses 53b. The light guide bundle 50A that is connected to the light source 5 runs through the endoscope 1 from a proximal end of each illumination lens 53b. Further, an illumination optical system includes the illumination windows 50b, 55b, and the illumination lens 53b, and illuminating light from the light guide bundle 50A, which is an illuminating member, passes through the illumination optical system.

A central axis LA3 (central axis of the illumination region of the illuminating light) of the illumination window 50b of the distal end face 10A of the second endoscope 1b is arranged at a position so as to be separated by a predetermined length Ld from an optical axis MA2 of the second observation window 15b. The illumination window 55b is arranged at a position so as to be separated by a predetermined length Le from the optical axis MA2 of the second observation window 15b. The central axis of the second observation window 15b coincides with the optical axis MA2 of the second observation optical system 21b. Further, the central axis of the illumination window 50b coincides with the central axis LA3 of the illuminating light, and the central axis of the illumination window 55b coincides with the central axis LA4 of the illuminating light. In other words, the central axis LA3 and the optical axis MA2 are separated by the predetermined length Ld, and the central axis LA4 and the optical axis MA2 are separated by the predetermined length Le. The lengths Ld and Le can be the same (Ld=Le), or can be different (Ld≠Le).

Further, at least one of the distances Ld and Le is longer than one of the lengths La and Lb that has the longest distance among the lengths La and Lb. Here, the length Ld is the separation between the illumination window 50b of the second endoscope 1b and the second observation window 15b, and the length Le is the separation between the illumination window 55b of the second endoscope 1b and the second observation window 15b. Further, the length La is the separation between the illumination window 50a of the first endoscope 1a and the first observation window 15a, and the length Lb is the separation between the illumination window 55a of the first endoscope 1a and the first observation window 15a. When the lengths La and Lb of the first endoscope 1a are the same (La=Lb), one of the lengths Ld and Le of the second endoscope 1b is longer than the lengths La and Lb of the first endoscope 1a (La=Lb<Ld or La=Lb<Le). When the lengths La and Lb of the first endoscope 1a are different (La≠Lb), one of the lengths Ld and Le of the second endoscope 1b is longer than one of the lengths La and Lb of the first endoscope 1a that is the longest among the lengths La and Lb (La<Ld, Lb<Ld or La<Le, Lb<Le).

As similar to the first endoscope 1a, the illuminating light that is supplied from the light source 5 is emitted from the two distal end faces of the light guide bundle 50A. Then, one of the two illuminating light having the central axis LA3 that passes through one of the two illumination lenses 53b is emitted from the illumination window 50b, and other illuminating light having the central axis LA4 that passes through other illumination lens 53b is emitted from the illumination window 55b.

The illumination lenses 53a, 53b, and the light guide bundle 50A of the first endoscope 1a and the second endoscope 1b of FIGS. 7 to 9 described hereinafter have the same aforementioned configuration. Thus, light flux of the illuminating light emitted from the two illumination lenses 53a of the first endoscope 1a is the same as light flux of the illuminating light emitted from the two illumination lenses 53b of the second endoscope 1b.

Furthermore, the light source 5 has a light intensity controlling unit, not shown, that modulates a preliminarily set predetermined light intensity of the illuminating light by detecting brightness of the observation image that is displayed on the monitor screen 7a. Here, the light intensity controlling unit automatically modulates the light intensity to increase or decrease.

Next, imaging faces on a plain face P1 at an arbitrary imaging distance L1 of the first endoscope 1a and the second endoscope 1b of the endoscope system 100 of the present embodiment is explained. The arbitrary imaging distance L1 is an arbitrary imaging distance between the window face on an observation side of the first observation window 15a of the first endoscope 1a and the plain face P1 that is orthogonal to the optical axis MA1 and between the window face on an observation side of the second observation window 15b of the second endoscope 1b and the plain face P1 that is orthogonal to the optical axis MA2.

When the first endoscope 1a shown in FIG. 5 images the plain face P1, a first imaging region A is displayed on the monitor screen 7a. The first imaging region A is a region corresponding to a field of view with the viewing angle α1 of the first endoscope 1a. Here, the region is shown by two radial dotted lines LR1 in FIG. 5. Further, as shown in FIG. 5, the first imaging region A on the plain face P1 at the arbitrary imaging distance L1 is included in an illumination region that is illuminated with the illuminating light having an illuminance that is greater than or equal to a predetermined illuminance. The illuminating light is emitted from the two illumination windows 50a and 55a, and shown by radial dotted lines LX1 and LX 2 in FIG. 5. The radial dotted line LX1 shows a boundary line of the predetermined illuminance of the illuminating light emitted from the illumination window 50a, and the radial dotted line LX2 shows a boundary line of the predetermined illuminance of the illuminating light emitted from the illumination window 55a. Hereinafter, the radial dotted line LX1 is referred to as a first boundary line LX1, and the radial dotted line LX2 is referred to as a second boundary line LX2.

When the second endoscope 1b shown in FIG. 6 images the plain face P1, a second imaging region B is displayed on the monitor screen 7a. The second imaging region B is a region within the viewing angle α2 of the second endoscope 1b. Here, the region is shown by two radial dotted lines LR2 in FIG. 6. As shown in FIG. 6, the imaging region B on the plain face P1 at the arbitrary imaging distance L1 is substantially included in an illumination region that is illuminated with the illuminating light having the illuminance that is greater than or equal to the predetermined illuminance. The illuminating light is emitted from the two illumination windows 50b and 55b, and shown by radial dotted lines LX3 and LX4 in FIG. 6. The radial dotted line LX3 shows a boundary line of the predetermined illuminance of the illuminating light emitted from the illumination window 50b, and the radial dotted line LX4 shows a boundary line of the predetermined illuminance of the illuminating light emitted from the illumination window 55b. Hereinafter, the radial dotted line LX3 is referred to as a third boundary line LX3, and the radial dotted line LX4 is referred to as a fourth boundary line LX4.

Further in details, each of the imaging regions A and B that are included in the illuminating light with the illuminance that is greater than or equal to the predetermined illuminance is explained with reference to FIGS. 7 to 9, when the plain face P1 at the arbitrary imaging distance L1 is imaged by the first endoscope 1a and the second endoscope 1b. The region that is displayed on the monitor screen 7a is explained further in details. FIG. 7 is a drawing illustrating a state in which the first imaging region A is displayed on the monitor screen 7a, and as the first imaging region A, the first endoscope 1a images the plain face P1 at the arbitrary imaging distance L1. FIGS. 8 and 9 are drawings illustrating a state in which the second imaging region B is displayed on the monitor screen 7a, and as the second imaging region B, the second endoscope 1b images the plain face P1 at the arbitrary imaging distance L1.

Figure 7:
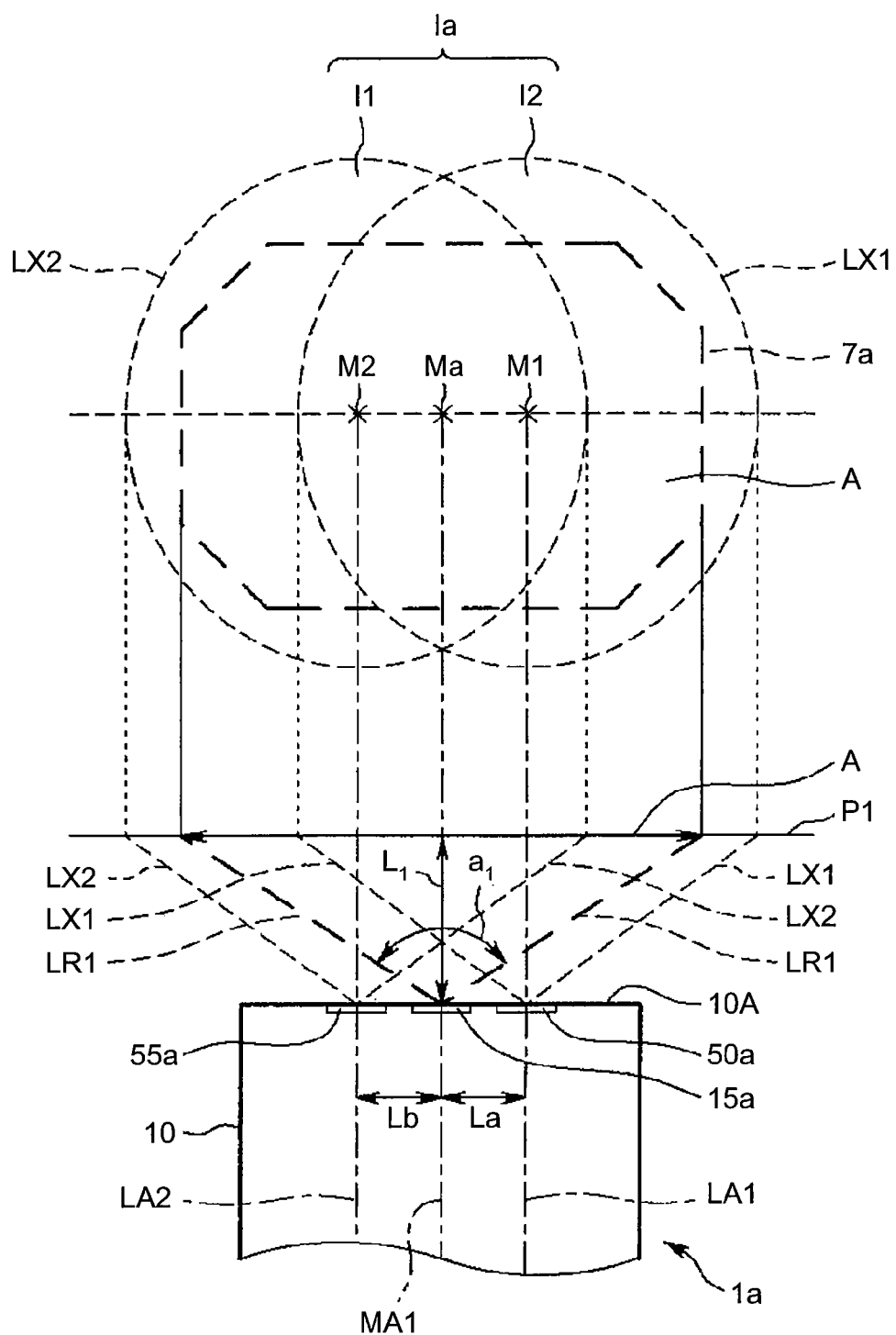
FIG. 7 is a drawing illustrating a state in which an imaging region is displayed on a monitor screen, and as the imaging region, the first endoscope images a plain face at an arbitrary imaging distance.

When the plain face P1 at the arbitrary imaging distance L1 is imaged by employing the first endoscope 1a, the first imaging region A that is displayed on the monitor screen 7a is included in the illumination region bounded by the first boundary line LX1 and the illumination region bounded by the second boundary line LX2, as shown in FIG. 7. Here, each illumination region is illuminated with the illuminating light having the illuminance that is greater than or equal to the predetermined illuminance. In more details, the first imaging region A is included in a first illumination region Ia, which is formed by illumination regions I1 and I2, having overall illuminance that is greater than or equal to the predetermined illuminance. The illumination region I1 is a light distribution region of the illuminating light, which is emitted from the illumination window 50a, with the illuminance that is greater than or equal to the predetermined illuminance, and the illumination region I2 has a point M1 through which the central axis LA1 passes. The illumination region I2 is a light distribution region of the illuminating light, which is emitted from the illumination window 55a, with the illuminance that is greater than or equal to the predetermined illuminance, and the illumination region I1 has a point M2 through which the central axis LA2 passes. Both of the light distribution regions are on the plain face P1. Further, one portion of the illumination region I1 and one portion of the illumination region I2 are superposed on each other. In other words, the entire first imaging region A of the first endoscope 1a at the arbitrary imaging distance L1 is illuminated with the illuminating light having the illuminance that is greater than or equal to the predetermined illuminance. Consequently, the entire image on the monitor screen 7a has brightness that is greater than or equal to the predetermined illuminance.

A letter Ma in FIG. 7 represents a point at which the optical axis MA1 of the first endoscope 1a intersects with the first imaging region A. Since the optical axis MA1 and the two central axes LA1 and LA2 are parallel to each other, the distance between the point Ma and the point M1 is the length La and the distance between the point Ma and the point M2 is the length Lb. Here, the points Ma, Mb, M1, and M2 are on the first imaging region A, which is on the plain face P1 at the imaging distance L1 of the first endoscope 1a.

Figure 8:
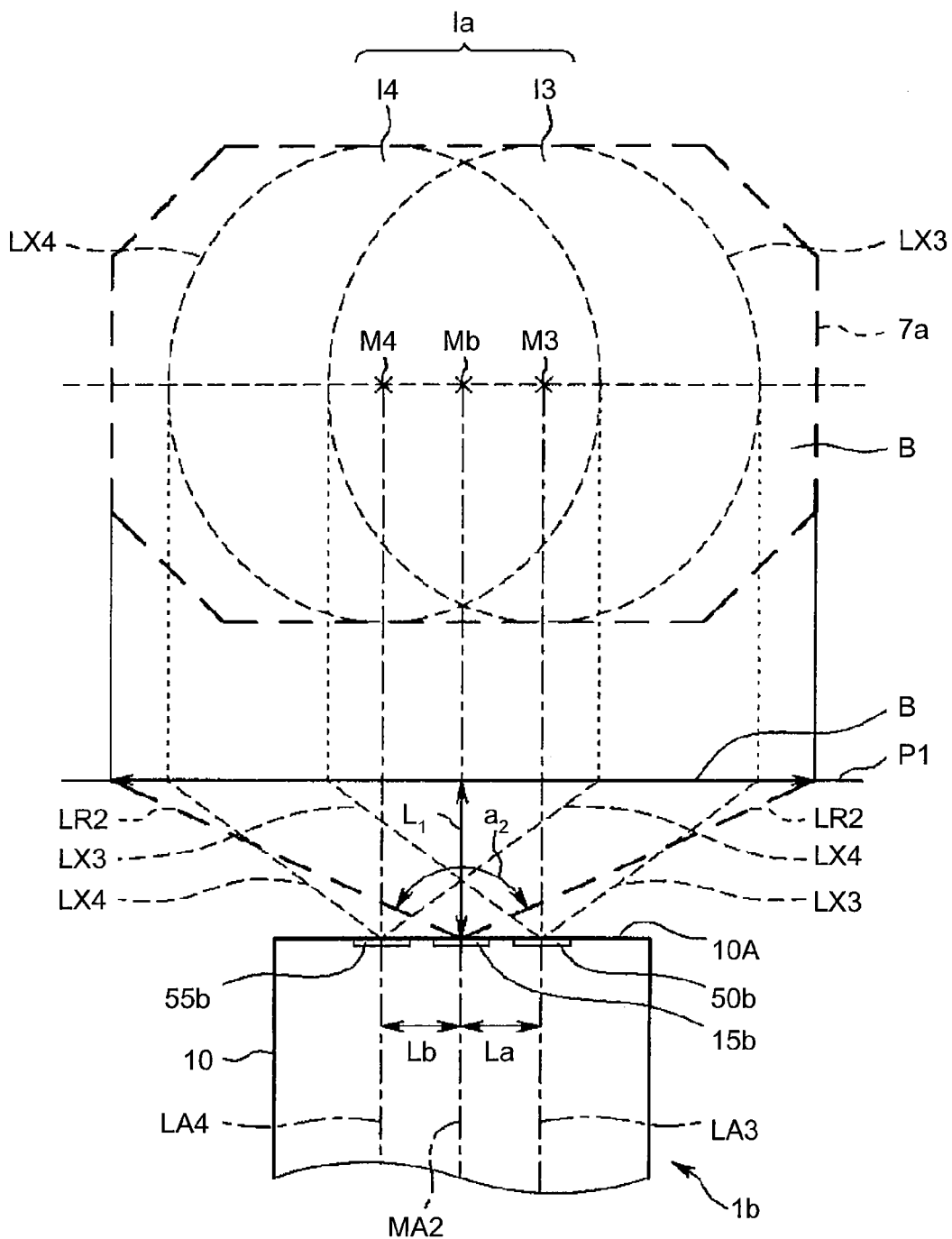
FIG. 8 is a drawing illustrating a state in which an imaging region is displayed on the monitor screen, and as the imaging region, the second endoscope 1b images the plain face at the arbitrary imaging distance.

As shown in FIG. 8, when the second endoscope 1b images the plain face P1 at the imaging distance L1, the second endoscope 1b can display the second imaging region B which is wider than the first imaging region A of the first endoscope 1a, on the monitor screen 7a, since the second endoscope 1b has the second observation optical system 21b with the viewing angle $\alpha 2$ which is wider than the viewing angle $\alpha 1$ of the first endoscope 1a.

Further, as shown in FIG. 8, a first illumination region Ia that is the same as the first illumination region Ia of the first endoscope 1a is formed on the plain face P1 of the second endoscope 1b when the second endoscope 1b has the two central axes LA3 and LA4 that are each separated from the optical axis MA2 by the lengths La and Lb, respectively. Here, the lengths La and Lb of the second endoscope 1b are the same as the lengths La and Lb of the first endoscope 1a, and the length La and Lb are the separations between the optical axis MA1 and each of the central axes LA1 and LA2, respectively. Therefore, a ratio in which the second imaging region B is included in the second illumination region Ib that is illuminated with the illuminating light having the illuminance that is greater than or equal to the predetermined illuminance by the second endoscope 1b is less than a ratio in which the first imaging region A is included in the first illumination region Ia that is illuminated with the illuminating light having the illuminance that is greater than or equal to the predetermined illuminance by the first endoscope 1a. In other words, the second endoscope 1b cannot illuminate a surrounding portion on the second imaging region B that is to be imaged with the illuminating light having the illuminance that is greater than or equal to the predetermined illuminance. Hence, the monitor screen 7a that is displayed by the second endoscope 1b displays the surrounding portion darker than the surrounding portion on the monitor screen 7a that is displayed by the first endoscope 1a.

Figure 9:
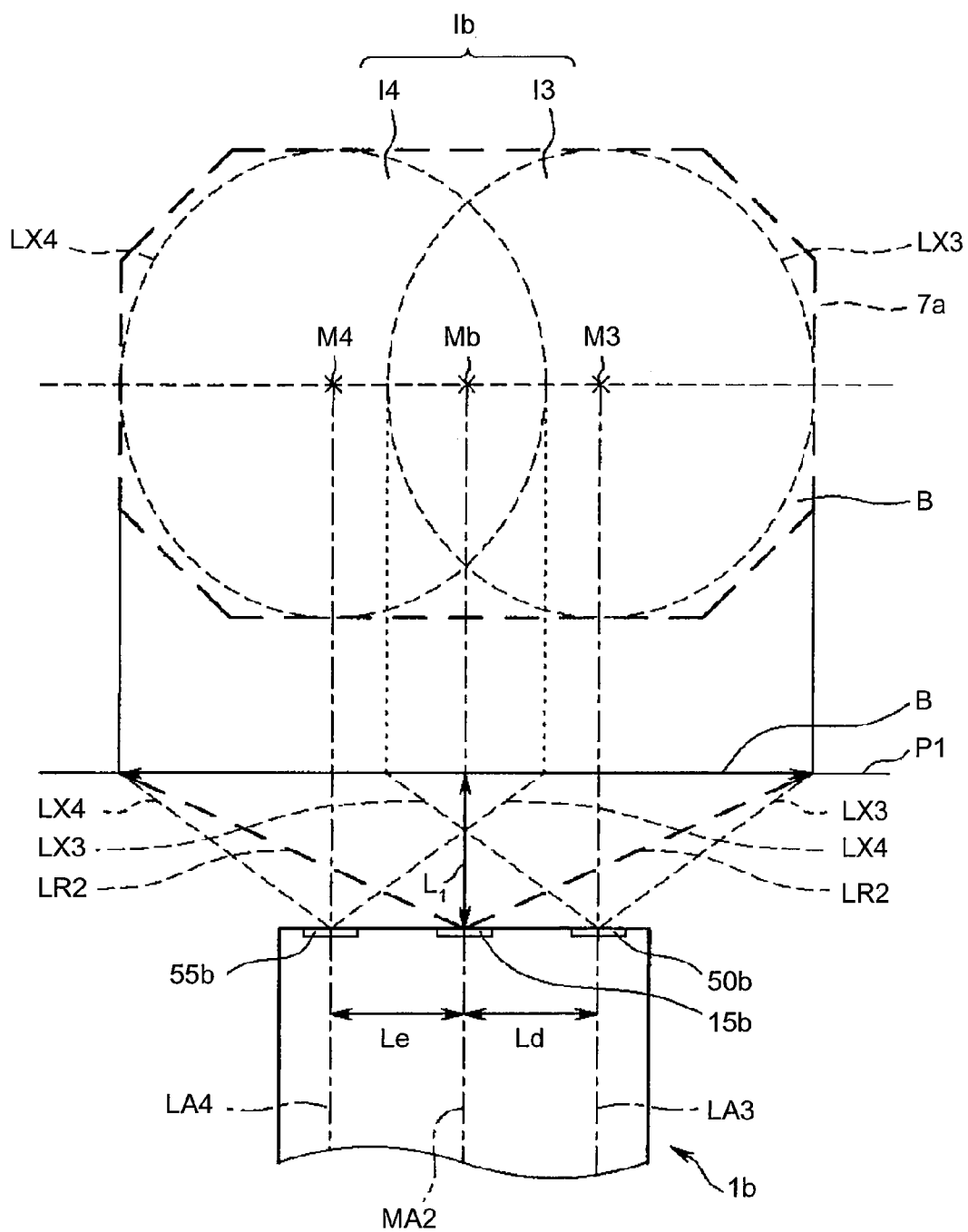
FIG. 9 is a drawing illustrating a state in which an imaging region is displayed on the monitor screen, and as the imaging region, the second endoscope 1b images the plain face at the arbitrary imaging distance.

Thus, as shown in FIG. 9, the distance between the optical axis MA2 and one of the central axes LA3 and LA4 of the second endoscope 1b is set to be longer than the longest distance among the distances between the optical axis MA1 and the central axis LA1 of the first endoscope 1a and between the optical axis MA1 and the central axis LA2 of the first endoscope 1a. The distances just mentioned are set as described above in order to substantially include the second imaging region B that is displayed on the display 7a in the illumination region that is bounded by the third boundary line LX3 and in the illumination region that is bounded by the fourth boundary line LX4. Here, each of the two illumination regions just mentioned is illuminated by the illuminating light having the illuminance that is greater than or equal to the predetermined illuminance. Particularly, the second imaging region B is substantially included in the second illumination region Ib in which the entire region thereof is illuminated with the illuminating light having the illuminance that is greater than or equal to the predetermined illuminance. The illumination region Ib is formed by an illumination region I3 and an illumination region I4. The illumination region I3 is a light distribution region of the illuminating light, which is emitted from the illumination window 50b onto the plain face P1, with the illuminance that is greater than or equal to the predetermined illuminance. The illumination region I4 is a light distribution region of the illuminating light, which is emitted from the illumination window 55b onto the plain face P1, with the illuminance that is greater than or equal to the predetermined illuminance. Further, the illumination region I3 has a point M3 through which the central axis LA3 passes, and the illumination region I4 has a point M4 through which the central axis LA4 passes. A portion of the illumination region I3 and a portion of the illumination region I4 are superposed on each other. Hence, in the second endoscope 1b, the distances between the optical axis MA2 and the central axis LA3 and between the optical axis MA2 and the central axis LA4 are determined in order to illuminate a surrounding portion on the second imaging region B of the second endoscope 1b at the arbitrary imaging distance L1 with the illuminating light having the illuminance that is greater than or equal to the predetermine illuminance. Then, positions of the second observation window 15b and the two illumination windows 50b and 55b, which are to be arranged on the distal end face 10A, are determined.

As a result, the second endoscope 1b can display the observation image so as to include the surrounding portion in the predetermined brightness that is substantially the same as the predetermined brightness on the monitor screen 7a that is displayed by the first endoscope 1a.

The letter Mb in FIG. 9 represents a point at which the optical axis MA2 of the second endoscope 1b intersects with the second imaging region B. Since the optical axis MA2 and the two central axes LA3 and LA4 are parallel to each other, the distance between the points Mb and M3 is the length Ld and the distance between the points Mb and M4 is the length Le. Here, the points Mb, M3, and M4 are on the second imaging region B, which is on the plain face P1 at the imaging distance L1 of the second endoscope 1b.

A relationship between the lengths Ld and Le of the second endoscope 1b with respect to the lengths La and Lb of the first endoscope 1a is described hereinafter. When the lengths La and Lb of the first endoscope 1a are the same (La=Lb), one of the lengths Ld and Le of the second endoscope 1b is longer than the lengths La and Lb of the first endoscope 1a (La=Lb<Ld or La=Lb<Le). When the lengths La and Lb are different (La≠Lb), one of the lengths Ld and Le of the second endoscope 1b is longer than one of the lengths La and Lb of the first endoscope 1a that is the longest among the lengths La and Lb (La<Ld, Lb<Ld or La<Le, Lb<Le).

Hence, the second illumination region Ib on the plain face P1 at the arbitrary imaging distance L1 of the second endoscope 1b is wider than the first illumination region Ia on the plain face P1 at the arbitrary imaging distance L1 of the first endoscope 1a. Thus, the second endoscope 1b can illuminate the illumination region, which is wider than the illumination region of the first endoscope 1a, on the plain face P1 at the arbitrary imaging distance L1 with the illuminating light having the illuminance that is greater than or equal to the predetermined illuminance.

As described hereinbefore, according to the endoscope system 100 of the present embodiment, the surrounding portion on the second imaging region B of the second endoscope 1b is illuminated with the illuminating light having the illuminance that is greater than or equal to the predetermined illuminance when the second endoscope 1b and the first endoscope 1a are employed. Here, the second endoscope 1b has the second observation optical system 21b having the viewing angle α2, and the first endoscope 1a has the first observation optical system 21a having the viewing angle α1. Therefore, the first imaging region A that is displayed on the monitor screen 7a by the first endoscope 1a and the second imaging region B that is displayed on the monitor screen 7a by the second endoscope 1b have substantially the same brightness.

Hence, the operator does not feel uncomfortableness due to the difference in the brightness at the surrounding portion on the image that is displayed on the monitor screen 7a when the second endoscope 1b is employed before/after employing the first endoscope 1a. In other words, the operator does not feel uncomfortableness due to the difference in the brightness at the surrounding portion on the monitor screen 7a when the second endoscope 1b is employed before/after employing the first endoscope 1a.

Figure 10:
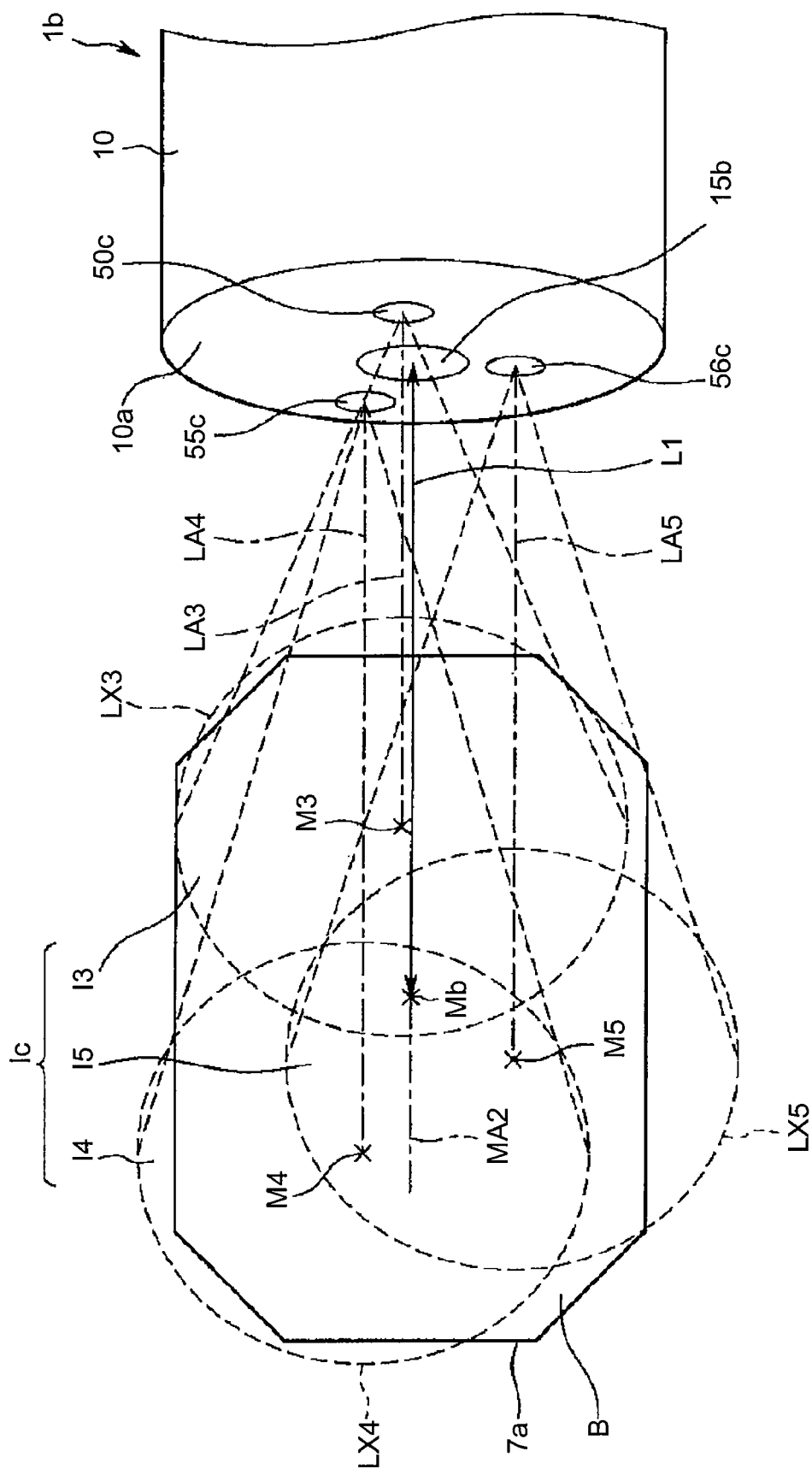
FIG. 10 is a drawing illustrating a state in which an imaging region at the arbitrary imaging distance is displayed on the monitor screen by the second endoscope.
Figure 11:
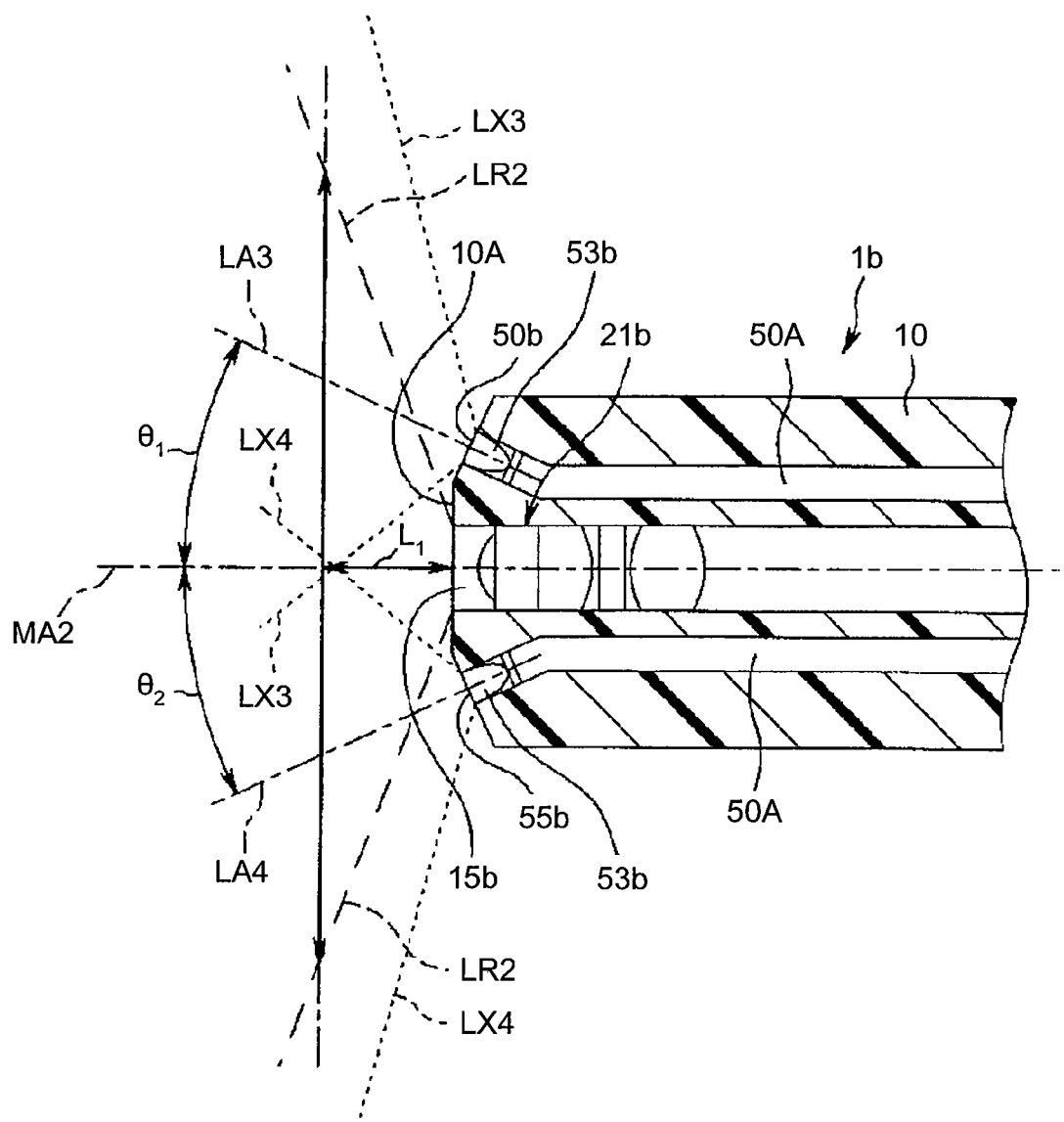
FIG. 11 is a longitudinal sectional view of a distal end portion of the second endoscope of a second embodiment along a plane passing through each center of window surfaces of illumination windows and a center of a window face of the second observation window.

As shown in FIG. 10, plural illumination windows can be arranged on the distal end face 10A of the distal end portion 10 of the second endoscope 1b, and three illumination windows 50c, 55c and 56c are arranged on the distal end face 10a in FIG. 10. FIG. 10 is a drawing illustrating a state in which the second imaging region B is displayed on the monitor screen 7a by the second endoscope 1b at the arbitrary imaging distance L1. Configurations, effects, and advantages of the second endoscope 1b and the monitor screen 7a in FIG. 11 are the same as those of the aforementioned second endoscope 1b and the monitor screen 7a. Therefore, explanations of the configurations, the effects, and the advantages are not to be repeated.

A radial dotted line LX5 of FIG. 10 shows a boundary line of a predetermined illuminance of illuminating light that is emitted from the illumination window 56c. Further, the radial dotted line LX5 is referred to as a fifth boundary line LX5.

A third illumination region Ic in which an entire region thereof is illuminated with the illuminating light having the illuminance that is greater than or equal to the predetermined illuminance is formed by an illumination region I5 and the illumination regions I3 and I4. The illumination region I5 is a region of the illuminating light, which is emitted from the illumination window 56c, with the illuminance that is greater than or equal to the predetermined illuminance. The illumination region I5 is on the second imaging region B, and the illumination region I5 has a point M5 through which a central axis LA5 passes. A plane of the second imaging region B is substantially included in a plane of the third illumination region Ic. Hence, in the second endoscope 1b, the distances between the optical axis MA2 and each of the central axes LA3, LA4, and LA5 are determined in order to illuminate a surrounding portion on the second imaging region B of the second endoscope 1b at the arbitrary distance L1 with the illuminating light having the illuminance that is greater than or equal to the predetermined illuminance. Then, positions of the second observation window 15b and the three illumination windows 50c, 55c, and 56c that are to be arranged on the distal end face 10a are determined.

As a result, the third illumination region Ic on the plain face P1 at the arbitrary imaging distance L1 of the second endoscope 1b is wider than the first illumination region Ia on the plain face P1 at the arbitrary distance L1 of the first endoscope 1a. In other words, the second endoscope 1b can illuminate the illumination region, which is wider than the illumination region of the first endoscope 1a, on the plain face P1 at the arbitrary imaging distance L1 with the illuminating light having the illuminance that is greater than or equal to the predetermined illuminance.

Figure 12:
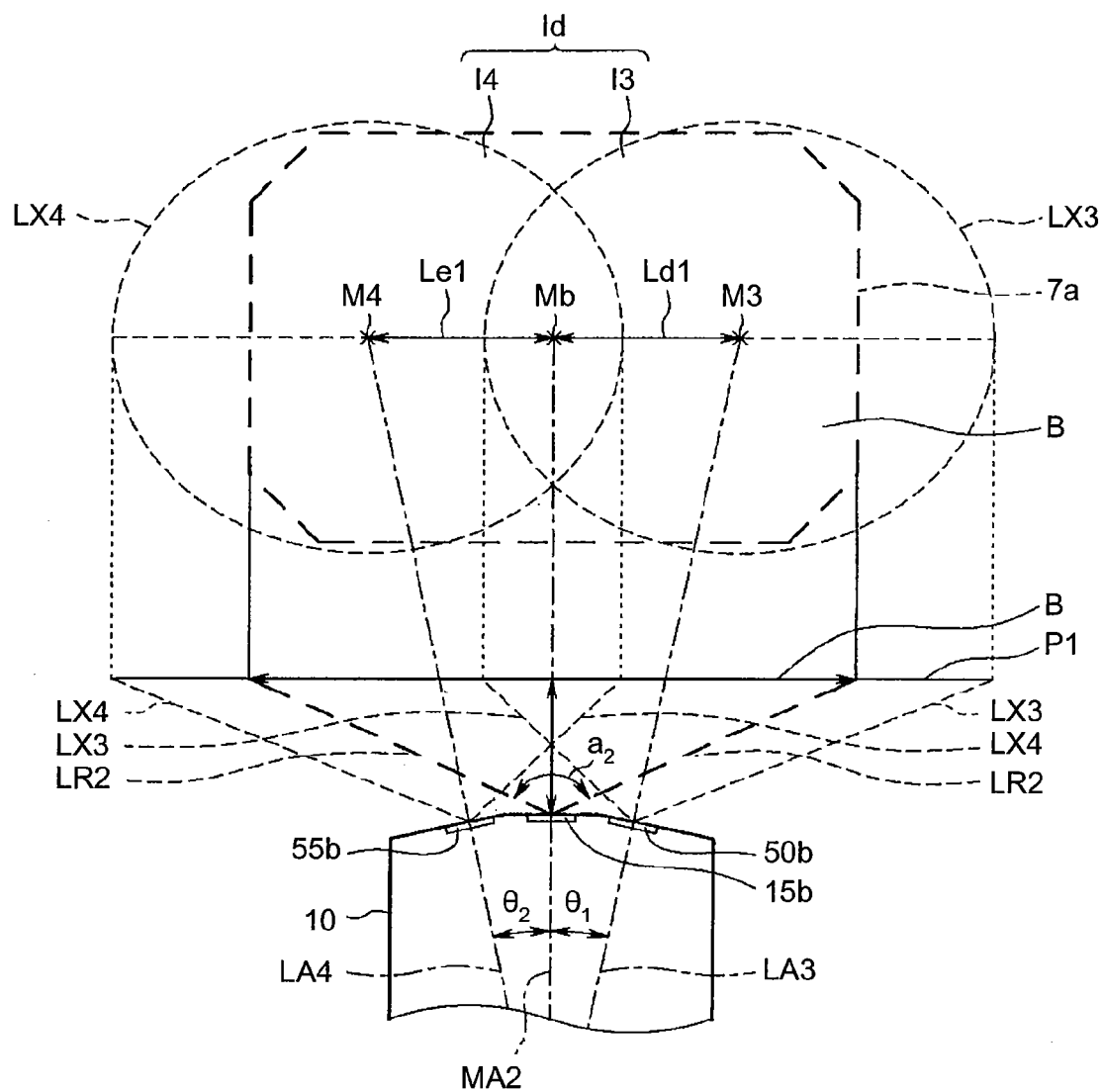
FIG. 12 is a drawing illustrating a state in which an imaging region is displayed on a monitor screen, and as the imaging region, the second endoscope at the arbitrary imaging distance images the plain face.

The endoscope system 100 according to the present embodiment is explained hereinafter with reference to FIGS. 11 and 12. FIG. 11 is a longitudinal sectional view of the distal end portion 10 of the second endoscope 1b along a longitudinal direction thereof along a plane passing through each of centers of window faces of the illumination windows 50b, 55b, and a center of a window face of the second observation window 15b. FIG. 12 is a drawing illustrating a state in which the second imaging region B is displayed on the monitor screen 7a, and as the second imaging region B, the second endoscope 1b images the plain face P1 at the arbitrary imaging distance L1.

Hereinafter, in an explanation of the endoscope system 100 of the present embodiment, the same letters and numerals that are the same as those of the first embodiment are affixed for configurations and effects that are the same as the configurations and the effects of the endoscope system 100 of the first embodiment. Then, explanations for the same configurations and effects are not to be repeated.

In FIG. 11, the second endoscope 1b has two illumination lenses 53b in which optical axes thereof are pointed towards a surrounding on the second imaging region B. In the present embodiment, the two illumination lenses 53b are arranged respectively at the two illumination windows 50b and 55b. More particularly, the second endoscope 1b has the central axes LA3 and LA4. The central axis LA3 is inclined with respect to the optical axis MA2 of the second observation optical system 21b by a predetermined angle of inclination θ1, and the central axis LA4 is inclined with respect to the optical axis MA2 of the second observation optical system 21b by a predetermined angle of inclination θ2.

Hence, the illumination window 50b through which the central axis LA3 passes has one window face with the angle of inclination θ1 and other window face with the angle of inclination θ2. The angle of inclination θ1 is an angle between the one window face and the window face of the second observation window 15b through which the optical axis MA2 passes. The angle of inclination θ2 is an angle between the other window face and the window face of the second observation window 15b through which the optical axis passes.

Next, the second imaging region B, which is included in the illuminating light with the illuminance that is greater than or equal to the predetermined illuminance when the plain face P1 at the arbitrary imaging distance L1 is imaged by the second endoscope 1b, is explained with reference to FIG. 12. Thus, a region that is displayed on the monitor screen 7a is explained.

As shown in FIG. 12, when the plain face P1 is imaged at the arbitrary imaging distance L1, the second imaging region B that is displayed on the monitor screen 7a is substantially included in an illumination region that is bounded by the third boundary line LX3 and an illumination region that is bounded by the fourth boundary line LX4. Here, each illumination region is illuminated with the illuminating light having the illuminance that is greater than or equal to the predetermined illuminance. Further, in the first endoscope 1a, the optical axis MA1 and the two central axes LA1 and LA2 are parallel to each other, so that the distances between the point Ma and each of the point M1 and the point M2 on the first imaging region A is the lengths La and Lb, respectively. The length La is the distance between the optical axis MA1 and the central axis LA1, and the length Lb is the distance between the optical axis MA1 and the central axis LA2. Therefore, by setting one of lengths Ld1 and Le1 to be longer than the longest length among the two lengths La and Lb, an area of the second illumination region Id that is formed by the illumination regions I3 and I4 of the second endoscope 1b can be set to be larger than an area of the first illumination region Ia of the first endoscope 1a. Here, the two lengths La and Lb are the distances between the optical axis MA1 of the first endoscope 1a and the central axes LA1 and LA2, respectively. Further, the two lengths Ld1 and Le1 are the distance between the point Mb and the points M3 and M4 on the second imaging region B of the second endoscope 1b, respectively. A relationship between the lengths Ld1 and Le1, with respect to the lengths La and Lb on the illumination region I1 of the first endoscope 1a, on the second illumination region Id of the second endoscope 1b is explained hereinafter. When the lengths La and Lb of the first endoscope 1a are the same (La=Lb), one of the lengths Ld1 and Le1 of the second endoscope 1b is longer than the lengths La and Lb of the first endoscope 1a (La=Lb<Ld1 or La=Lb<Le1). When the lengths La and Lb are different (La≠Lb), one of the lengths Ld1 and Le1 of the second endoscope 1b is longer than the longest distance among the lengths La and Lb of the first endoscope 1a (La<Ld1, Lb<Ld1 or La<Le1, Lb<Le1).

The second illumination region Id on the plain face P1 at the arbitrary imaging distance L1 of the second endoscope 1b is wider than the first illumination region Ia on the plain face P1 at the arbitrary imaging distance L1 of the first endoscope 1a. Hence, the second endoscope 1b can illuminate the illumination region, which is wider than the illumination region of the first endoscope 1a, on the plain face P1 at the arbitrary imaging distance L1 with the illuminating light having the illuminance that is greater than or equal to the predetermined illuminance. Hence, the second endoscope 1b can display the image on the monitor screen 7a so that the second endoscope 1b substantially includes the surrounding portion in the predetermined brightness that is substantially the same as the brightness on the monitor screen 7a that is displayed by the first endoscope 1a.

As a result, the endoscope system 100 of the present embodiment can obtain the effect that is the same as the effect of the endoscope system 100 of the first embodiment.

In the first and the second embodiments, the illumination region may be illuminated with illuminating light having an angle of illumination that is wider than an angle of illumination of the illuminating light of the first endoscope 1a. Here, the second endoscope 1b has at least one illumination optical system that can illuminate the illumination region, which is wider than the illumination region of the illuminating light having the illuminance that is greater than or equal to the predetermined illuminance of the first endoscope 1a, with the illuminating light having the illuminance that is greater than or equal to the predetermined illuminance. Furthermore, a diode, which is a light emitting element, can be employed as the illumination member arranged at the distal ends of the endoscopes 1a and 1b. Here, the diode illuminates the illumination region with the illuminating light having the illuminance that is greater than or equal to the predetermined illuminance, and the illuminating light has a central axis of the illumination region at the arbitrary imaging distance L1.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system, comprising:
   a first endoscope having a first observation optical system with a first viewing angle and a first illumination optical system; and
   a second endoscope having a second observation optical system with a second viewing angle wider than the first viewing angle and a second illumination optical system;
   a display unit that displays a first image of a body cavity obtained through the first endoscope and a second image of a body cavity obtained through the second endoscope, wherein
   a second illumination region of illuminating light that is emitted by the second illumination optical system and has a predetermined illuminance is wider than a first illumination region of illuminating light that is emitted by the first illumination optical system and has a predetermined illuminance, at any imaging distance that is pointed in an observation direction from a distal end of an insertion portion of each of the first endoscope and the second endoscope, so that a surrounding portion of the first image and a surrounding portion of the second image are displayed at substantially the same brightness by the display unit.

2. The endoscope system according to claim 1, wherein the first endoscope includes
- at least two illumination optical systems in the first illumination optical system, and
- the first illumination region that is formed by illumination regions of the at least two illumination optical systems, the second endoscope includes
- plural illumination optical systems in the second illumination optical system, and
- the second illumination region that is formed by illumination regions of the plural illumination optical systems, and the second illumination region is made wider than the first illumination region by setting a longest distance among distances between an optical axis of the second observation optical system and central axes of the illumination regions longer than a longest distance among distances between an optical axis of the first observation optical system and central axes of the illumination regions, the optical axis of the first observation optical system being parallel to the central axes of the illumination optical systems of the first endoscope, and the optical axis of the second observation optical system being parallel to the central axes of the illumination optical systems of the second endoscope.

3. The endoscope system according to claim 1, wherein a number of the illumination optical systems in the second endoscope is larger than a number of the illumination optical systems in the first endoscope so that the second illumination region is made wider than the first illumination region.

4. The endoscope system according to claim 1, wherein an angle of inclination between an optical axis of the second observation optical system and at least one of central axes of the illumination regions among the central axes running within the second illumination region is set wider than any one of angles of inclination between an optical axis of the first observation optical system and the central axes running within the first illumination region, so that the second illumination region is made wider than the first illumination region.

5. The endoscope system according to claim 2, wherein the plural illumination optical systems include at least three illumination optical systems.

* * * * *